US012236934B2

(12) United States Patent
Pang et al.

(10) Patent No.: US 12,236,934 B2
(45) Date of Patent: Feb. 25, 2025

(54) COMPOUND ACOUSTIC LENS

(71) Applicant: FUJIFILM SONOSITE, INC., Bothell, WA (US)

(72) Inventors: Guofeng Pang, Bothell, WA (US); Oleg Ivanytskyy, Bothell, WA (US); Robert Kolaja, Bothell, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 63 days.

(21) Appl. No.: 17/555,111

(22) Filed: Dec. 17, 2021

(65) Prior Publication Data

US 2023/0197056 A1   Jun. 22, 2023

(51) Int. Cl.
*G10K 11/30* (2006.01)
*A61B 8/00* (2006.01)

(52) U.S. Cl.
CPC ............ *G10K 11/30* (2013.01); *A61B 8/4494* (2013.01)

(58) Field of Classification Search
CPC ..................................................... G10K 11/30
See application file for complete search history.

(56) References Cited

U.S. PATENT DOCUMENTS

2003/0053915 A1 *   3/2003   Keilman ................ F04B 35/00
                                                                  417/322
2017/0112473 A1 *   4/2017   Samset ................ A61B 8/5246

FOREIGN PATENT DOCUMENTS

JP        H-0763465         *   7/1995
WO    WO-2022102276 A1   *   5/2022   ............. G10K 11/30

OTHER PUBLICATIONS

Engholm, Mathias et al. "Increasing the Field-of-View of Row-column-Addressed Ultrasound Transducers: Implementation of a Diverging Compound Lens." Ultrasonics 88 (2018): 97-105. Web. (Year: 2018).*

* cited by examiner

*Primary Examiner* — Joseph M Santos Rodriguez
*Assistant Examiner* — Tommy T Ly
(74) *Attorney, Agent, or Firm* — Womble Bond Dickinson (US) LLP (57) ABSTRACT

A compound acoustic lens, an ultrasound probe and a medical device that includes the same are described. In some embodiments, a compound acoustic lens for an ultrasound probe includes an outer lens including a first material of a first thickness, and an inner lens mated to the outer lens. The inner lens includes a second material of a second thickness. The overall thickness of the compound acoustic lens is determined as a sum of the first thickness and the second thickness and is less than a thickness of a single-material lens having a same focal length as the compound acoustic lens.

17 Claims, 7 Drawing Sheets

COMPOUND ACOUSTIC LENS

FIELD OF THE INVENTION

The embodiments disclosed herein relate generally to ultrasound transducers; more specifically, the embodiments disclosed herein relate to ultrasound transducers having compound lenses.

BACKGROUND

Transducers, such as acoustic transducers, are used in medical imaging where an acoustic probe transmits and receives ultrasound waves to create images of the internal tissues of a patient. An acoustic lens is a device that redirects and focuses acoustic waves. It is a layer of material attached to the very front surface of an acoustic stack. The focused acoustic waves have a better sensitivity and improve the resolution of imaging.

In order to obtain the desired acoustic waveform and improve the imaging resolution, the acoustic probes include an acoustic lens to focus the acoustic beam produced by the transducers. The material of such a lens is usually made of silicone, plastic or other elastomer. Silicone has been widely used in low frequency ultrasound transducers because of the relatively low acoustic attenuation. However, the acoustic loss of silicone increases significantly as the operating frequency increases. It also cuts off the bandwidth. Plastic is a good candidate because of its very low acoustic loss even in the ultra-high frequency range of 15-50 MHz. However, in that case, its shape has to be concave due to the much faster speed of sound than water. Generally speaking, the radius of the concaved lens might be as small as 5.4 mm in a 20 MHz transducer, and decreases rapidly as the operating frequency increases. Therefore, a lens thickness of at least more than 0.5 millimeter (500 microns) is required to maintain the elevation width. In the case where there is a requirement to produce kerf cuts into the lens, it becomes impossible to cut through such a thick layer. The foregoing assumes a kerf width of no more than 10 microns.

Manufacturers are limited to producing lenses having a single layer at present, and the only way to produce a focused acoustic beam is to provide a curved outer surface. Thus, the current state of the art cannot produce a focused beam transducer having a flat outer surface.

SUMMARY

A compound acoustic lens, an ultrasound probe and a medical device that includes the same are described. In some embodiments, a compound acoustic lens for an ultrasound probe includes an outer lens including a first material of a first thickness, and an inner lens mated to the outer lens. The inner lens includes a second material of a second thickness. The overall thickness of the compound acoustic lens is determined as a sum of the first thickness and the second thickness and is less than a thickness of a single-material lens having a same focal length as the compound acoustic lens.

In some embodiments, an ultrasound probe includes a transducer array and a compound acoustic lens coupled to the transducer array. The compound acoustic lens includes an outer lens including a first material of a first thickness and an inner lens mated to the outer lens. The inner lens including a second material of a second thickness. The overall thickness of the compound acoustic lens is determined as a sum of the first thickness and the second thickness, with the overall thickness being less than 380 micrometers.

In some embodiments, a medical device includes an ultrasound probe having a compound acoustic lens, a memory storing instructions, and a processor system coupled to the memory and the ultrasound probe. Upon execution of the instructions, the processor system is configured to cause the ultrasound probe to transmit an ultrasound beam through the compound acoustic lens that focuses the ultrasound beam. The compound acoustic lens has an outer lens including a first material of a first thickness, and an inner lens mated to the outer lens, where the inner lens includes a second material of a second thickness. The overall thickness of the compound acoustic lens is determined from the first thickness and the second thickness, and is less than a thickness of a single-material lens having a same focal length as the compound acoustic lens.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

A compound acoustic lens for an ultrasound probe and method for fabricating the same are disclosed. In some embodiments, the compound acoustic lens includes an outer lens and an inner lens mated to each other. In some embodiments, the outer lens and the inner lens are curved so that the compound acoustic lens functions as a concave lens. In some embodiments, the inner lens includes a first material (e.g., silicone, etc.) of a first thickness, while the outer lens includes a second material (e.g., Rexolite, etc.) of a second thickness. The overall thickness of the compound acoustic lens can be determined from the sum of the first thickness and the second thickness and is less than a thickness of a single-material lens having a same focal length as the compound acoustic lens. In some embodiments, a distal end of the outer lens includes a flat surface for patient contact.

Figure 1:
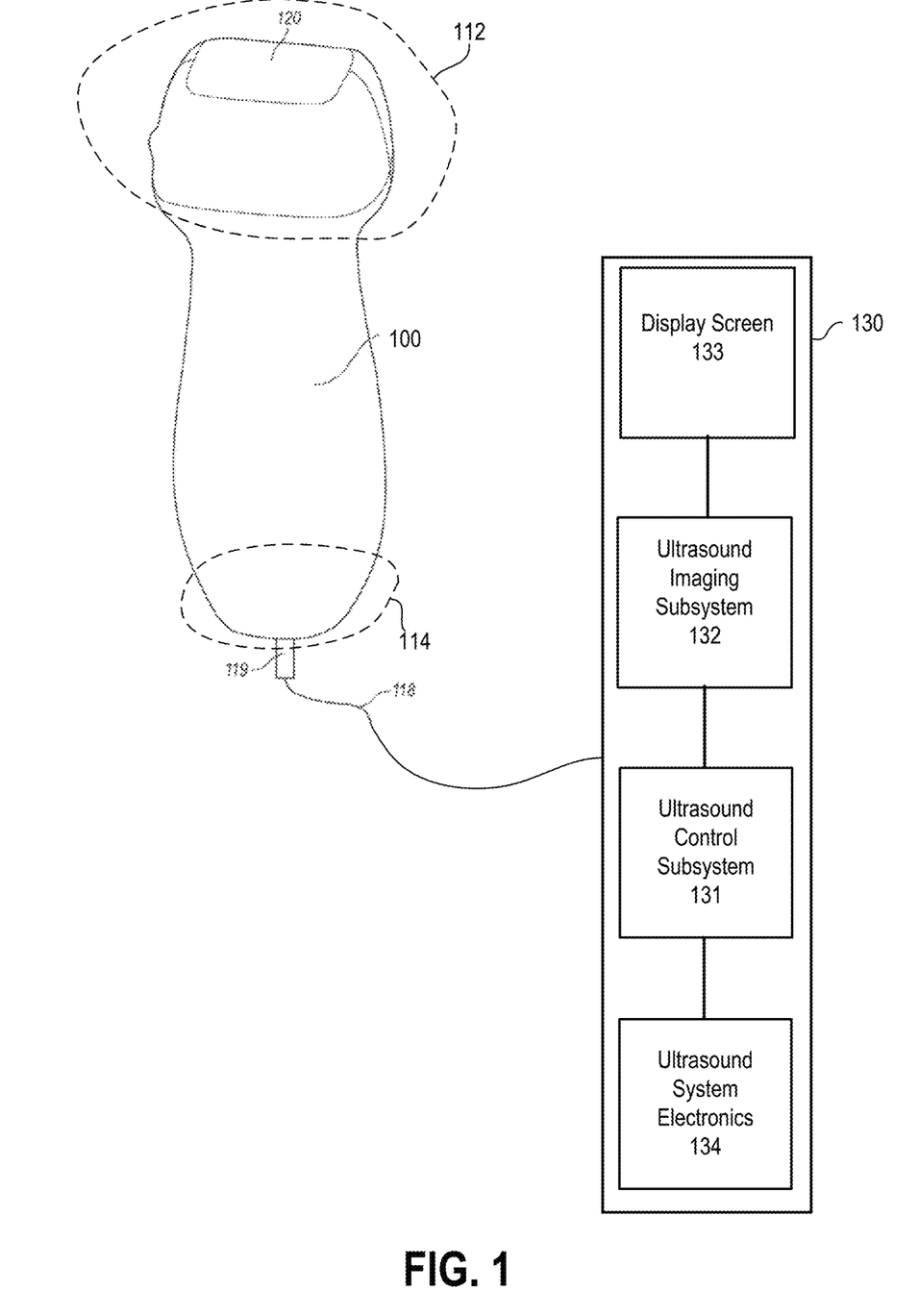
FIG. 1 illustrates some embodiments of an ultrasound transducer probe having an ultrasound transducer assembly.

FIG. 1 illustrates some embodiments of an ultrasound transducer probe having an ultrasound transducer assembly configured in accordance with an embodiment of the disclosed technology. Referring to FIG. 1, ultrasound transducer probe 100 includes an enclosure extending between a distal end portion 112 and a proximal end portion 114. The ultrasound transducer probe 100 is electrically coupled to an ultrasound imaging system 130 that includes ultrasound control subsystem 131, ultrasound imaging subsystem 132, display screen 133, and ultrasound system electronics 134. The transducer probe 100 is electrically coupled to the ultrasound imaging system 130 via a cable 118 that is attached to the proximal end of the probe by a strain relief element 119. Additionally or alternatively, the ultrasound probe 100 can be electrically coupled to the ultrasound imaging system 130 via a wireless communication link.

A transducer assembly 120 having one or more transducer elements is electrically coupled to the ultrasound system electronics 134 in ultrasound imaging system 130. In operation, transducer assembly 120 transmits ultrasound energy from the one or more transducer elements toward a subject and receives ultrasound echoes from the subject. The ultrasound echoes are converted into electrical signals by the one or more transducer elements and electrically transmitted to the ultrasound system electronics 134 in ultrasound imaging system 130 to form one or more ultrasound images.

Capturing ultrasound data from a subject using an exemplary transducer assembly (e.g., the transducer assembly 120) generally includes generating ultrasound, transmitting ultrasound into the subject, and receiving ultrasound reflected by the subject. A wide range of frequencies of ultrasound can be used to capture ultrasound data, such as, for example, low frequency ultrasound (e.g., less than 15 MHz) and/or high frequency ultrasound (e.g., greater than or equal to 15 MHz) can be used. Those of ordinary skill in the art can readily determine which frequency range to use based on factors such as, for example, but not limited to, depth of imaging and/or desired resolution.

In some embodiments, ultrasound imaging system 130 includes ultrasound system electronics 134 that comprises one or more processors, integrated circuits, ASICs, FPGAs, and power sources to support the functioning of ultrasound imaging system 130 in a manner well-known in the art. In some embodiments, ultrasound imaging system 130 also includes ultrasound control subsystem 131 having one or more processors. At least one processor can cause electrical signals to be sent to the transducer(s) of probe 100 to emit sound waves and also receive the electrical pulses from the probe that were created from the returning echoes. One or more processors can process the raw data associated with the received electrical pulses and form an image that is sent to ultrasound imaging subsystem 132, which can display the image on display screen 133. Thus, display screen 133 can display ultrasound images from the ultrasound data processed by the processor of ultrasound control subsystem 131.

In some embodiments, the ultrasound imaging system 130 also has one or more user input devices (e.g., a keyboard, a cursor control device, etc.) that inputs data and allows the taking of measurements from the display of the ultrasound display subsystem. The ultrasound imaging system 130 can include one or more output devices, such as a disk storage device (e.g., hard, floppy, thumb drive, compact disks (CD), digital video discs (DVDs)) for storing the acquired images, and a printer that prints the image from the displayed data. These input and output devices have not been shown in FIG. 1 to avoid obscuring the techniques disclosed herein.

In some embodiments, the ultrasound transducer assembly 120 comprises a transducer layer configured to emit ultrasound energy, one or more matching layers overlaying the transducer layer, a thermally conductive layer overlaying the one or more matching layers, and a lens overlaying the thermally conductive layer. In some embodiments, the lens is a compound acoustic lens for an ultrasound transducer assembly having an ultra-high frequency phase array. In such a case, in some embodiments, the processor-based system coupled to the memory and the ultrasound probe, upon execution of the instructions, causes the ultrasound probe to transmit an ultrasound beam through the compound acoustic lens that focuses the ultrasound beam.

In some embodiments, the compound lens consists of two layers of materials. In some embodiments, the two layers of material comprise Rexolite 1422 and Fujifilm LLL-9 silicone, respectively. Fujifilm LLL-9 silicone, herein after to referred to as "LLL-9", is developed by and available from Medical Systems Research & Development Center, FUJIFILM Corporation, 798, Miyanodai, Kaiseimachi, Ashigarakami-gun, KANAGAWA 258-8538, JAPAN LLL-9 has a lower acoustic attenuation than that of RTV630, a traditional silicone. LLL-9 also demonstrates a superior bandwidth when operating at the same frequency range compared to traditional silicone. LLL-9 and similar silicones may be used for the compound acoustic lenses described herein.

In some embodiments, the compound acoustic lens is created by creating a concaved curvature on one material (e.g., the Rexolite surface) using a lens forming technique developed in-house in Fujifilm Visualsonics Inc., Toronto (VSI). Alternatively, the concaved curvature on the one material may be formed on a computer numerical control (CNC) machine. After forming the concaved curvature on the one material, the second material (e.g., silicone, LLL-9) is then cast on top of the first material (e.g., Rexolite, plastic, etc.) using a molding technique. In some embodiments, prior to casting the second material onto the first material with the concaved curvature, the concaved curvature surface is pre-treated to enable the two materials to more strongly adhere to each other. In some embodiments, the molding technique involves setting up a structure around the location where the second material is to be placed and placing the material within the gap created by the structure. In some embodiments, the structure includes a flat surface (e.g., a flat metal surface) at the top or distal end of the second material farthest from the first material in order to create a flat outer lens surface. Thereafter, the structure is removed. Note other molding and non-molding techniques can be used to deposit or otherwise place the second material onto the first material.

Figure 2A:
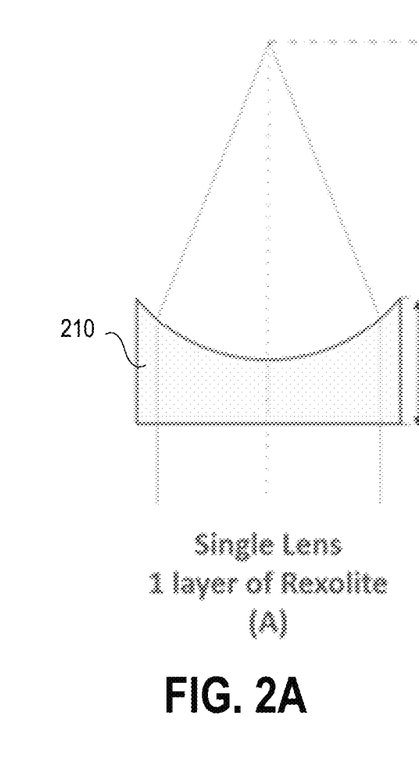
FIGS. 2A-F illustrate diagrams of acoustic focal paths using single lenses and a compound lens.
Figure 2B:
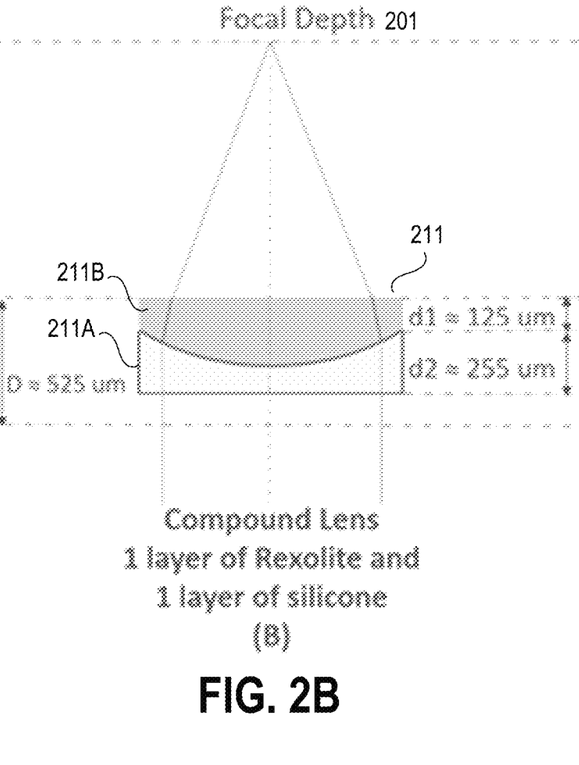
Figure 2C:
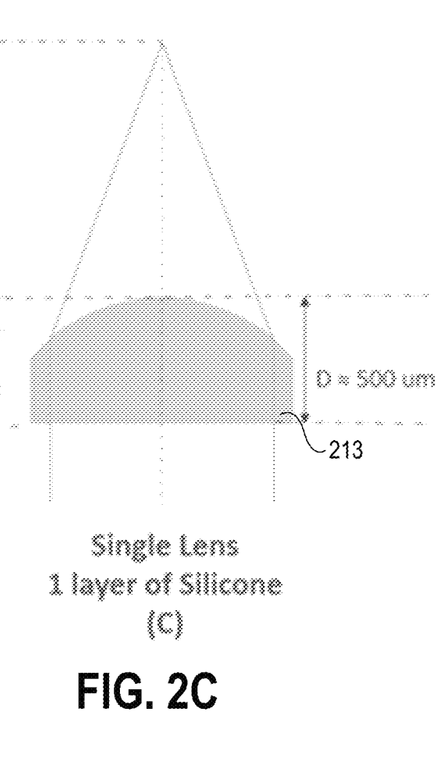

FIGS. 2A-C illustrate diagrams of acoustic focal paths using single lenses and a compound acoustic lens described herein. FIG. 2A shows a single lens 210 having a concave shape and made of one layer of Rexolite. Lens 210 produces an acoustic focal path when used with an ultrasound transducer that is focused at focal depth 201. In this example, the height of lens 210 at its outer edges is approximately 525 μm and the ultrasound transducer operates at 20 MHz. FIG. 2C shows a single lens 213 having a convex shape and made of one layer of silicone. Lens 213 produces an acoustic focal path when used with a 20 MHz ultrasound transducer that is focused at focal depth 201 as well. In this case, the height of lens 213 at its most central location is approximately 500 μm.

FIG. 2B shows a compound lens 211 with a flat top surface and made of a stack consisting of an inner lens made of Rexolite layer 211A and an outer lens of silicone layer 211B. Rexolite layer 211A has a concave shape while silicone layer 211B has a bottom side in a convex shape that is adjacent and matches the shape to the top of layer 211A. Silicone layer 211B has a flat top surface at its distal end that faces focal depth 201. In some embodiments, the outer lens and the inner lens are curved with a radius of curvature of at least 10 millimeters where they mate with each other so that the compound acoustic lens functions as a concave lens.

Compound lens 211 produces an acoustic focal path that is focused at focal depth 201. In one example embodiment, the height of layer 211A at its outer edges is approximately 255 µm and the height of layer 211B at its outer edges is approximately 125 µm. By Snell's Law, acoustic waves are refracted twice when passing through the compound lens stack of layers 211A and 211B as illustrated in FIG. 2B. This double refraction is due in part because the speed of sound in the Rexolite material is larger than the speed of sound in the silicone material, which prevents divergence of an ultrasound beam generated by the ultrasound probe having the compound lens. The redirected acoustic waves will converge at the same focal depth 201 as those emitted from the single lens shown in FIGS. 2A and 2C.

Producing such a compound lens provides several key advantages. Firstly, Rexolite layer 211A of compound lens 211 is relatively thinner than that of a single lens design. The thinness makes it viable to dice through thin Rexolite layer 211A by laser ablation or saw dicing. Secondly, the resultant flat outer surface of silicone layer 211B provides the user with a lens that is less likely to entrap air bubbles as compared to a concave lens, which results in better image quality. Thirdly, the acoustic attenuation of compound lens 211 is much less than that of a single lens 213 made entirely of silicone as shown in FIG. 2C.

The overall thickness of the compound lens is based on the thickness of each of the materials of the two lenses, where the thickness of the outer, or top, lens material (e.g., silicone) is measured along its left or right flat edge and the thickness of the inner, or bottom, lens material (e.g., Rexolite) is measured along a flat left or right edge of the inner, or bottom lens material. In some embodiments, the overall thickness of the compound lens is no greater than 380 micrometers. In some embodiments, the thickness of the silicone is no greater than 125 micrometers and the thickness of the Rexolite is no greater than 255 micrometers.

Figure 2D:
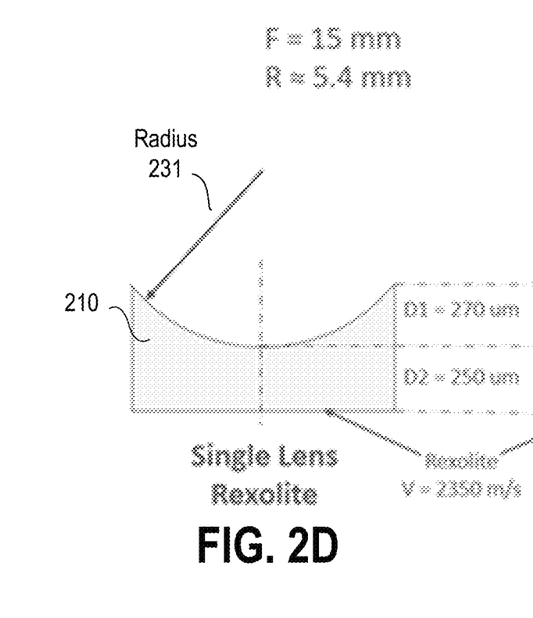
Figure 2E:
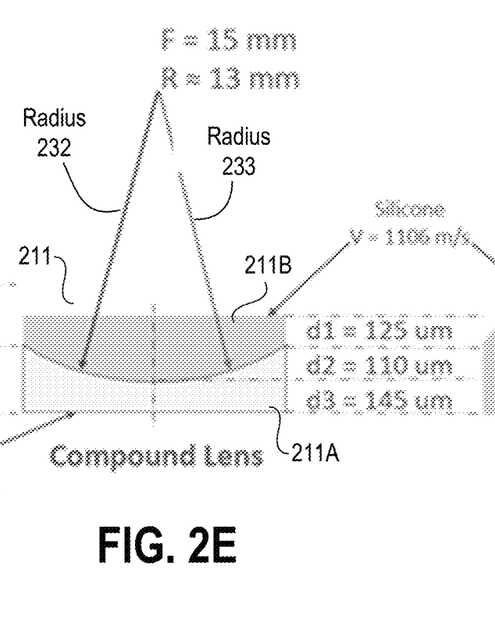
Figure 2F:
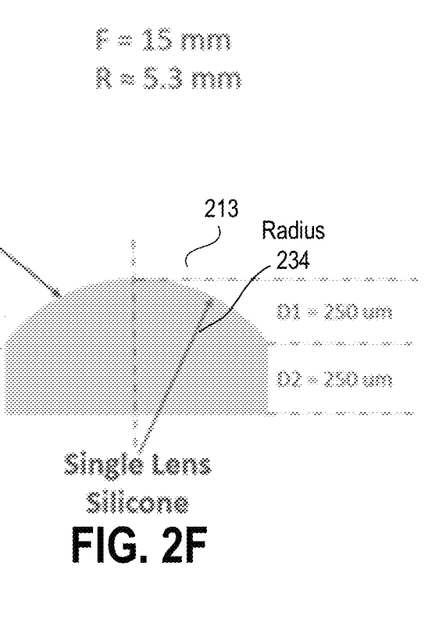

FIGS. 2D-2F illustrate an example embodiments of the acoustic compound lens and the lenses of FIGS. 2A-2C. Referring to FIGS. 2D-2F, the focal length (F) and radius of curvature (R) are shown for each of the lenses. For example, radius 231 and radius 232 are shown for the concave lens (e.g., Rexolite) in FIGS. 2D and 2E, while radius 233 and radius 234 are shown for the silicon portion of the compound lens and silicon lens in FIGS. 2E and 2F, respectively. Table 1 lists the technical perimeters of the lenses in FIGS. 2D-2F when used with a 20 MHz ultrasound transducer.

TABLE 1

Technical parameters of single acoustic lens and compound acoustic lens

| Parameters | Single Lens 210 | Compound Lens 211 | | Single Lens 213 |
|---|---|---|---|---|
| Material | Rexolite | Rexolite | Silicone | Silicone |
| Total Thickness | 525 microns | 255 microns | 235 microns | ~500 microns |
| Central Thickness | 250 microns | 145 microns | 235 microns | ~500 microns |
| Radius of | 5.4 mm | 13 mm | 13 mm | 5.3 mm |

TABLE 1-continued

Technical parameters of single acoustic lens and compound acoustic lens

| Parameters | Single Lens 210 | Compound Lens 211 | Single Lens 213 |
|---|---|---|---|
| Curvature Focal Depth | 15 mm | 15 mm | 15 mm |

In some embodiments, the array stack of an ultrasound probe including transducers and one or more matching layers are designed into a planar structure. In some embodiments, components of such an array stack are produced sequentially layer-by-layer. The addition of a compound lens will not significantly add manufacturing difficulty into the process. The fabrication method of the planar array structure with compound lenses can be applied to arrays having a broad range of operating frequencies. In such a case, any cutting of kerfs as part of creating a linear phased array is made possible using the two layers of different materials for the compound lens.

In some embodiments, the curvature of the Rexolite lens of the compound acoustic lens, as well as any layer(s) on top the Rexolite lens, is created to enable the ultrasound wave to be focused to a given depth in the imaging field. In some embodiments, in order to obtain the desired curvature, a two-stage lens forming process can be used.

Figure 3:
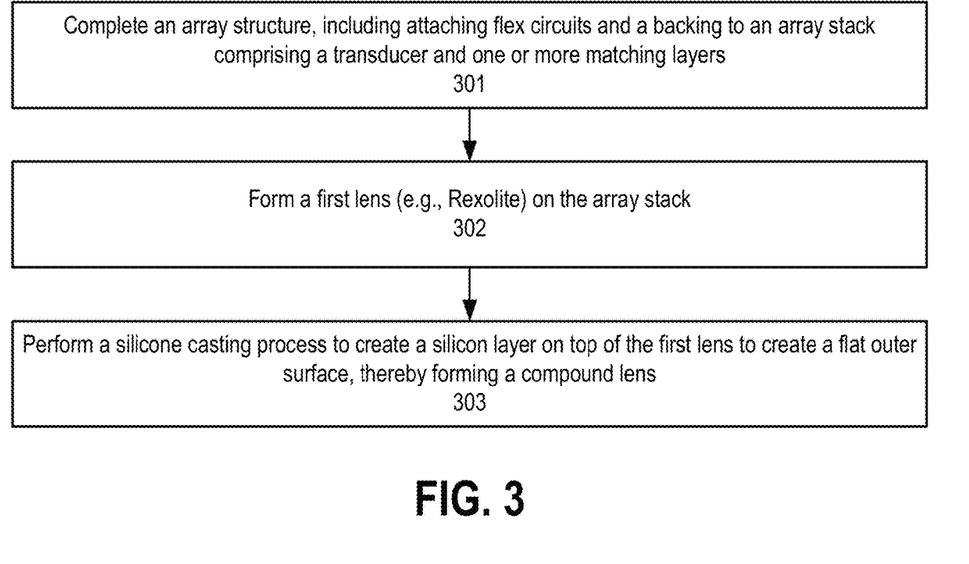
FIG. 3 is a flow diagram of some embodiments of a process for forming a compound lens.

FIG. 3 is a flow diagram of some embodiments of a process for forming a compound lens. The process can be performed by processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, fabrication apparatus that manufactures ultrasound lenses and probes. Such a system may include brackets or other devices to hold and assemble parts, as well as a robotic arm to pick up and transfer a compound lens or parts thereof during assembly and components to perform molding and casting functions describe herein.

Referring to FIG. 3, the process includes completing an array structure, including attaching flex circuits and a backing to an array stack comprising a transducer and one or more matching layers (processing block 301). Next, processing logic forms a first lens on the array stack (processing block 302). In some embodiments, lens forming is performed by holding the array within a fixture while a cutting tool is directed across a lens surface in a manner that creates a lens of the desired radius and depth. In some embodiments, the first lens includes Rexolite. Additionally or alternatively, other materials can be used for forming the first lens.

After forming the first lens, processing logic performs a silicone casting process to create a silicone layer on top of the first lens to create a flat outer surface, thereby creating a compound lens (processing block 303). In some embodiments, the silicone layer includes LLL-9. In some embodiments, the silicone casting process is a molding process that molds a silicone layer atop the first lens. In some embodiments, the silicone casting layer operates as a second lens to operate with the first lens to direct ultrasound energy to a focal depth.

Figure 4A:
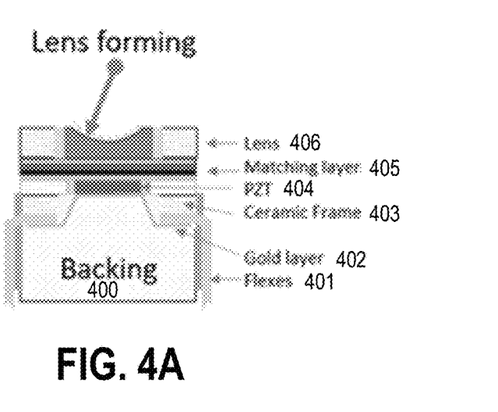
FIGS. 4A and 4B illustrate the process of forming a compound lens of FIG. 3.
Figure 4B:
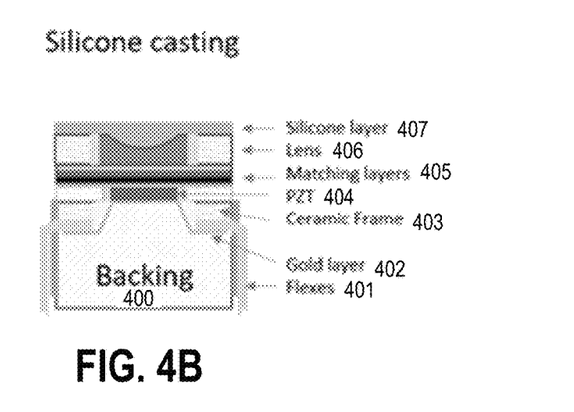

FIGS. 4A and 4B illustrate the process of forming a compound lens of FIG. 3. Refer to FIGS. 4A and 4B, backing 400 is coupled to a metal layer 402 (e.g., gold layer, etc.), frame 403 (e.g., ceramic frame, etc.), and transducer 404 (e.g., piezoelectric transducer (e.g., lead zirconate titanate, PZT)). Note that electrical connections to transducer 404 have not been shown to avoid obscuring the invention. Flexes 401 are coupled to metal layer 402. Matching layers 405 are coupled to the top of transducer 404. Lens 406 is attached to matching layers. After attachment, lens 406 undergoes a formation process in which a concave surface is created on the top part of the lens. The concave surface has a desired radius and depth based on the focal length that is desired (and achieved once the silicone is attached over the concave region of lens 406). After lens forming is completed as shown in FIG. 4A, the silicone casting process occurs in which silicone layer 407 is deposited on lens 406 in a form that it has a top flat surface.

Figure 5:
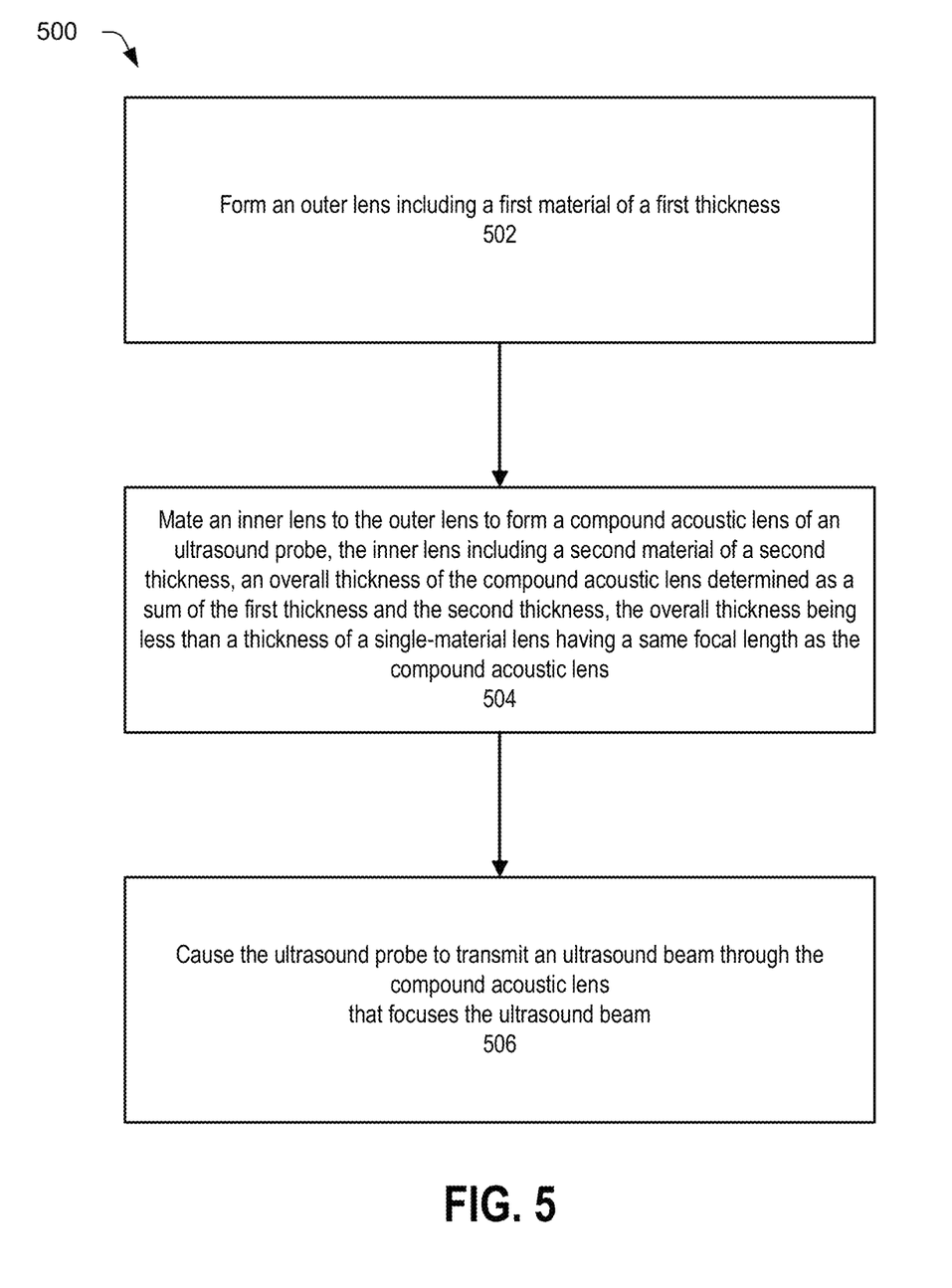
FIG. 5 is a flow diagram of some embodiments of a process for controlling an ultrasound probe with an acoustic lens.

FIG. 5 is a flow diagram of some embodiments of a process for controlling an ultrasound probe with an acoustic lens. The process can be performed by processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, fabrication apparatus that manufactures ultrasound lenses and probes. Such a system may include brackets or other devices to hold and assemble parts, as well as a robotic arm to pick up and transfer a compound lens or parts thereof during assembly and components to perform molding and casting functions describe herein.

Referring to FIG. 5, the process comprises forming an outer lens including a first material of a first thickness (502). In some embodiments, the first material includes silicone. After forming the outer lens, an inner lens mates to the outer lens to form a compound acoustic lens of the ultrasound probe (504). In some embodiments, the inner lens includes a second material of a second thickness. In some embodiments, the second material includes Rexolite. In some embodiments, a distal end of the outer lens includes a flat surface for patient contact.

In some embodiments, the outer lens and the inner lens are curved so that the compound acoustic lens functions as a concave lens. In some embodiments, a speed of sound in the first material is less than the speed of sound in the second material. In some embodiments, the outer lens and the inner lens are curved with a radius of curvature of at least 10 millimeters where the outer lens mates with the inner lens.

In some embodiments, the overall thickness of the compound acoustic lens is determined as the sum of the first and second thicknesses, and the overall thickness is less than a thickness of a single-material lens having a same focal length as the compound acoustic lens. In some embodiments, the overall thickness is no greater than 380 micrometers. In some embodiments, the first thickness is no greater than 125 micrometers and the second thickness is no greater than 255 micrometers, the first thickness measured along a first flat edge of the outer lens and the second thickness measured along a second flat edge of the inner lens.

Thereafter, the ultrasound probe with the compound acoustic lens may be used to transmit an ultrasound beam through the compound acoustic lens that focuses the ultrasound beam (506). In some embodiments, the ultrasound probe is part of a medical device comprising a memory storing instructions and a processor system coupled to the memory and the ultrasound probe that, upon execution of the instructions, is configured to cause the ultrasound probe to transmit an ultrasound beam through the compound acoustic lens that focuses the ultrasound beam.

Figure 6:
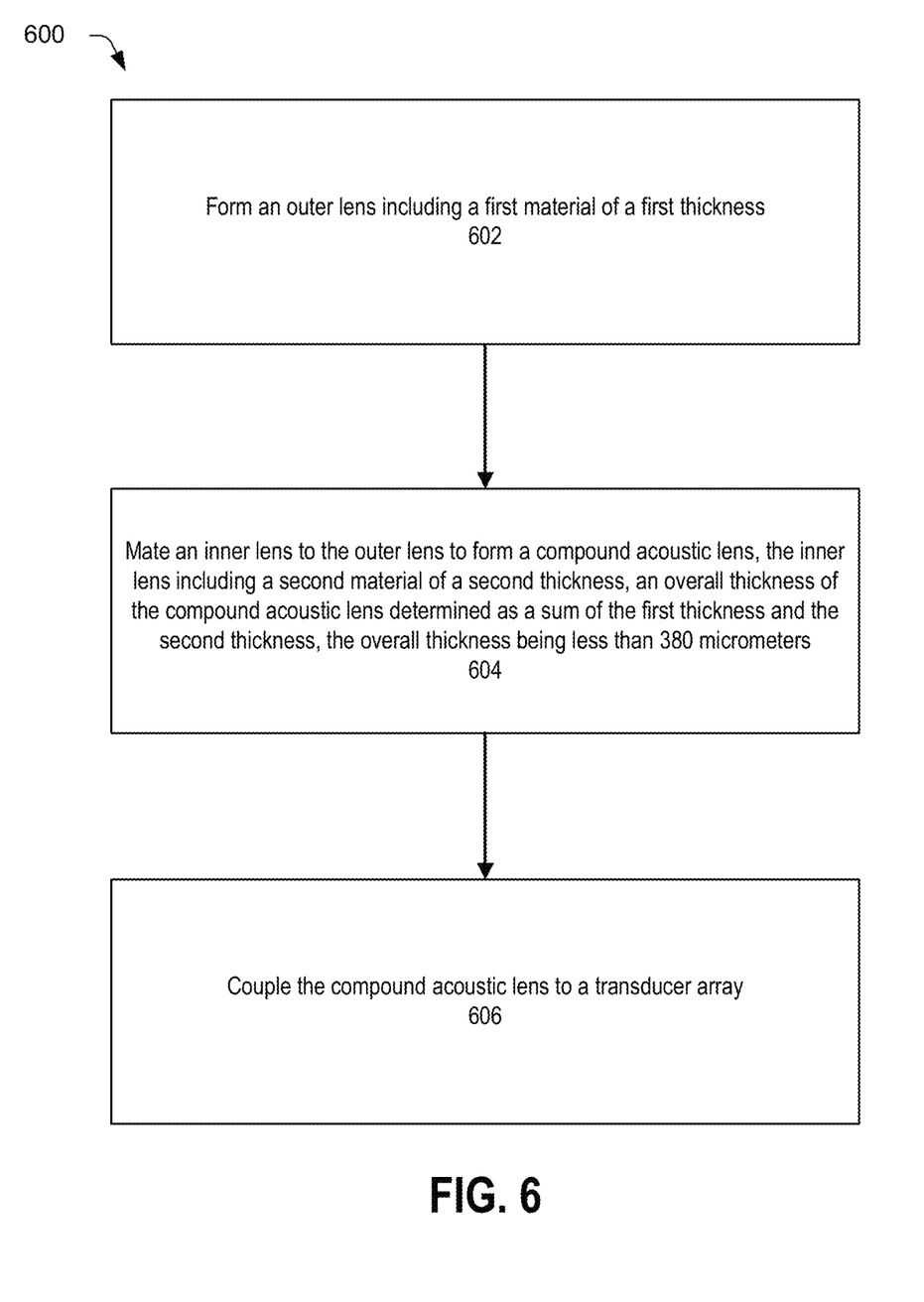
FIG. 6 is a flow diagram of some embodiments of a process for making an ultrasound probe with a compound acoustic lens

FIG. 6 is a flow diagram of some embodiments of a process for making an ultrasound probe with a compound acoustic lens. The process can be performed by processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, fabrication apparatus that manufactures ultrasound lenses and probes. Such a system may include brackets or other devices to hold and assemble parts, as well as a robotic arm to pick up and transfer a compound lens or parts thereof during assembly and components to perform molding and casting functions describe herein.

Referring to FIG. 6, the process comprises forming an outer lens including a first material of a first thickness (602). In some embodiments, the first material includes silicone. After forming the outer lens, an inner lens mates to the outer lens to form a compound acoustic lens of the ultrasound probe (604). In some embodiments, the inner lens includes a second material of a second thickness. In some embodiments, the second material includes Rexolite. In some embodiments, a distal end of the outer lens includes a flat surface for patient contact.

In some embodiments, the overall thickness of the compound acoustic lens is determined as the sum of the first and second thicknesses, and the overall thickness is less than a thickness of a single-material lens having a same focal length as the compound acoustic lens. In some embodiments, the overall thickness is no greater than 380 micrometers. In some embodiments, the first thickness is no greater than 125 micrometers and the second thickness is no greater than 255 micrometers, where the first thickness measured along a first flat edge of the outer lens and the second thickness measured along a second flat edge of the inner lens.

In some embodiments, the outer lens and the inner lens are curved so that the compound acoustic lens functions as a concave lens. In some embodiments, a speed of sound in the first material is less than the speed of sound in the second material, preventing divergence of an ultrasound beam generated by the ultrasound probe. In some embodiments, the outer lens and the inner lens are curved with a radius of curvature of at least 10 millimeters where the outer lens mates with the inner lens.

After mating the inner lens to the outer lens, the compound acoustic lens is coupled to the transducer array (606). In some embodiments, the compound acoustic lens is coupled to the transducer array with one or more matching layers. In some embodiments, the transducer array includes a piezoelectric transducer.

There is a number of example embodiments described herein.

Example 1 is a compound acoustic lens for an ultrasound probe, where the compound acoustic lens comprises: an outer lens including a first material of a first thickness; and an inner lens mated to the outer lens, where the inner lens includes a second material of a second thickness. The overall thickness of the compound acoustic lens is determined as a sum of the first thickness and the second thickness and is less than a thickness of a single-material lens having a same focal length as the compound acoustic lens.

Example 2 is the compound acoustic lens of example 1 that may optionally include that the first material includes silicone and the second material includes Rexolite.

Example 3 is the compound acoustic lens of example 1 that may optionally include that the outer lens and the inner lens are curved so that the compound acoustic lens functions as a concave lens.

Example 4 is the compound acoustic lens of example 3 that may optionally include that a speed of sound in the first material is less than the speed of sound in the second material.

Example 5 is the compound acoustic lens of example 1 that may optionally include that the overall thickness is no greater than 380 micrometers.

Example 6 is the compound acoustic lens of example 5 that may optionally include that the first thickness is no greater than 125 micrometers and the second thickness is no greater than 255 micrometers, the first thickness measured along a first flat edge of the outer lens and the second thickness measured along a second flat edge of the inner lens.

Example 7 is the compound acoustic lens of example 1 that may optionally include that a distal end of the outer lens includes a flat surface for patient contact.

Example 8 is the compound acoustic lens of example 1 that may optionally include that the outer lens and the inner lens are curved with a radius of curvature of at least 10 millimeters where the outer lens mates with the inner lens.

Example 9 is an ultrasound probe comprising: a transducer array; and a compound acoustic lens coupled to the transducer array. The compound acoustic lens includes: an outer lens including a first material of a first thickness; and an inner lens mated to the outer lens, the inner lens including a second material of a second thickness, an overall thickness of the compound acoustic lens determined as a sum of the first thickness and the second thickness, the overall thickness being less than 380 micrometers.

Example 10 is the ultrasound probe of example 9 that may optionally include that the overall thickness is less than a thickness of a single-material lens having a same focal length as the compound acoustic lens.

Example 11 is the ultrasound probe of example 9 that may optionally include that the compound acoustic lens is coupled to the transducer array with one or more matching layers.

Example 12 is the ultrasound probe of example 9 that may optionally include that the transducer array includes a piezoelectric transducer.

Example 13 is the ultrasound probe of example 9 that may optionally include that the first material includes silicone and the second material includes Rexolite, and the outer lens and the inner lens are curved to determine the compound acoustic lens as concave.

Example 14 is the ultrasound probe of example 13 that may optionally include that a speed of sound in the first material is less than the speed of sound in the second material, preventing divergence of an ultrasound beam generated by the ultrasound probe.

Example 15 is the ultrasound probe of example 9 that may optionally include that the outer lens and the inner lens are curved with a radius of curvature of at least 10 millimeters where the outer lens mates with the inner lens.

Example 16 is the ultrasound probe of example 9 that may optionally include that the first thickness is no greater than 125 micrometers and the second thickness is no greater than 255 micrometers, the first thickness measured along a first flat edge of the outer lens and the second thickness measured along a second flat edge of the inner lens.

Example 17 is the ultrasound probe of example 9 that may optionally include that a distal end of the outer lens includes a flat surface for patient contact.

Example 18 is a medical device comprising: an ultrasound probe having a compound acoustic lens; a memory storing instructions; and a processor system coupled to the memory and the ultrasound probe that, upon execution of the instructions, is configured to: cause the ultrasound probe to transmit an ultrasound beam through the compound acoustic lens that focuses the ultrasound beam, the compound acoustic lens having: an outer lens including a first material of a first thickness; an inner lens mated to the outer lens, the inner lens including a second material of a second thickness; and an overall thickness determined from the first thickness and the second thickness, the overall thickness being less than a thickness of a single-material lens having a same focal length as the compound acoustic lens.

Example 19 is the medical device of example 18 that may optionally include that the first material includes silicone and the second material includes Rexolite, and the outer lens and the inner lens are curved to determine the compound acoustic lens as concave.

Example 20 is the medical device of example 18 that may optionally include that the first material includes Rexolite and the second material includes silicone, and the outer lens and the inner lens are curved with a radius of curvature of at least 10 millimeters where the outer lens mates with the inner lens.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

We claim:

1. A compound acoustic lens for an ultrasound probe, the compound acoustic lens comprising:
   a silicone layer having a first flat surface, a convex surface, and a first thickness between the first flat surface and the convex surface; and
   a Rexolite layer having a second flat surface, a concaved surface, and a second thickness between the second flat surface and the concaved surface, wherein the concaved surface of the Rexolite layer is directly on and mated to the convex surface of the silicone layer, wherein each of the convex surface of the silicone layer and the concaved surface of the Rexolite layer is curved with a first radius of curvature where the convex surface of the silicone layer mates with the concaved surface of the Rexolite layer for the compound acoustic lens to focus acoustic waves generated by the ultrasound probe at a first focal length, and wherein the first radius of curvature is at least 10 millimeters that is greater than a second radius of curvature of a single material lens consisting of one of the Rexolite layer and the silicone layer having a second focal length that is the same as the first focal length to increase an operating frequency of the ultrasound probe.

2. The compound acoustic lens as described in claim 1, wherein a speed of sound in the silicone layer is less than the speed of sound in the Rexolite layer to prevent divergence of the acoustic waves generated by the ultrasound probe.

3. The compound acoustic lens as described in claim 1, wherein the first thickness is no greater than 125 micrometers and the second thickness is no greater than 255 micrometers, the first thickness measured along a first side edge of the silicone layer and the second thickness measured along a second side edge of the Rexolite layer.

4. The compound acoustic lens as described in claim 1, wherein the first flat surface of the silicone layer is for a patient contact, and the second flat surface of the Rexolite layer is to couple to a transducer array.

5. The compound acoustic lens as described in claim 1, wherein the first thickness is at a center of the silicone layer and the second thickness is at a center of the Rexolite layer, and wherein an overall thickness of the compound acoustic lens determined as a sum of the first thickness and the second thickness is less than the thickness at a center of a single material lens of one of the Rexolite layer and the silicone layer having the same focal length as the compound acoustic lens.

6. The compound acoustic lens as described in claim 5, wherein the overall thickness of the compound acoustic lens is less than 380 micrometers.

7. An ultrasound probe comprising:
a transducer array; and
a compound acoustic lens coupled to the transducer array, the compound acoustic lens including:
a silicone layer having a first flat surface, a convex surface and a first thickness between the first flat surface and the convex surface; and
a Rexolite layer having a second flat surface a concaved surface and a second thickness between the second flat surface and the concaved surface, wherein the concaved surface of the Rexolite layer is directly on and mated to the convex surface of the silicone layer, wherein each of the convex surface of the silicone layer and the concaved surface of the Rexolite layer is curved with a first radius of curvature where the convex surface of the silicone layer mates with the concaved surface of the Rexolite layer for the compound acoustic lens to focus acoustic waves generated by the ultrasound probe at a first focal length, and wherein the first radius of curvature is at least 10 millimeters that is greater than a second radius of curvature of a single material lens consisting of one of the Rexolite layer and the silicone layer having a second focal length that is the same as the first focal length to increase an operating frequency of the ultrasound probe.

8. The ultrasound probe as described in claim 7, wherein the second flat surface of the Rexolite layer is coupled to the transducer array via one or more matching layers.

9. The ultrasound probe as described in claim 7, wherein the transducer array includes a piezoelectric transducer.

10. The ultrasound probe as described in claim 7, wherein a speed of sound in the silicone layer is less than the speed of sound in the Rexolite layer to prevent divergence of the acoustic waves generated by the ultrasound probe.

11. The ultrasound probe as described in claim 7, wherein the first thickness is no greater than 125 micrometers and the second thickness is no greater than 255 micrometers, the first thickness measured along a first side edge of the silicone layer and the second thickness measured along a second side edge of the Rexolite layer.

12. The ultrasound probe as described in claim 7, wherein the first flat surface of the silicone layer is for a patient contact, and the second flat surface of the Rexolite layer is on one or more matching layers of the transducer array.

13. The ultrasound probe as described in claim 7, wherein the first thickness is at a center of the silicone layer and the second thickness is at a center of the Rexolite layer, and wherein an overall thickness of the compound acoustic lens determined as a sum of the first thickness and the second thickness is less than the thickness at a center of a single material lens of one of the Rexolite layer and the silicone layer having the same focal length as the compound acoustic lens.

14. The ultrasound probe as described in claim 13, wherein the overall thickness of the compound acoustic lens is less than 380 micrometers.

15. A medical device comprising:
an ultrasound probe having a compound acoustic lens;
a memory storing instructions; and
a processor system coupled to the memory and the ultrasound probe that, upon execution of the instructions, is configured to:
cause the ultrasound probe to transmit an ultrasound beam through the compound acoustic lens that focuses the ultrasound beam, the compound acoustic lens having:
a silicone layer having a first flat surface, a convex surface and a first thickness between the first flat surface and the convex surface;
a Rexolite layer having a second flat surface, a concaved surface, and a second thickness between the second flat surface and the concaved surface, wherein the concaved surface of the Rexolite layer is directly on and mated to the convex surface of the silicone layer, wherein each of the convex surface of the silicone layer and the concaved surface of the Rexolite layer is curved with a first radius of curvature where the convex surface of the silicone layer mates with the concaved surface of the Rexolite layer for the compound acoustic lens to focus acoustic waves generated by the ultrasound probe at a first focal length, and wherein the first radius of curvature is at least 10 millimeters that is greater than a second radius of curvature of a single material lens consisting of one of the Rexolite layer and the silicone layer having a second focal length that is the same as the first focal length to increase an operating frequency of the ultrasound probe.

16. The medical device as described in claim 15, wherein the first thickness is at a center of the silicone layer and the second thickness is at a center of the Rexolite layer, and wherein an overall thickness of the compound acoustic lens determined as a sum of the first thickness and the second thickness is less than the thickness at a center of a single material lens of one of the Rexolite layer and the silicone layer having the same focal length as the compound acoustic lens.

17. The medical device as described in claim 16, wherein the overall thickness of the compound acoustic lens is less than 380 micrometers.

\* \* \* \* \*